United States Patent
Abe et al.

(10) Patent No.: US 7,810,784 B2
(45) Date of Patent: Oct. 12, 2010

(54) ROLLER CLAMP

(75) Inventors: Kazuhiro Abe, Fukuroi (JP); Ichiro Kitani, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 886 days.

(21) Appl. No.: 11/682,715

(22) Filed: Mar. 6, 2007

(65) Prior Publication Data

US 2007/0272886 A1 Nov. 29, 2007

(30) Foreign Application Priority Data

Mar. 8, 2006 (JP) ............................. 2006-062337

(51) Int. Cl.
*F16K 7/04* (2006.01)
(52) U.S. Cl. ................. 251/6; 251/4; 604/34; 604/250; 138/45
(58) Field of Classification Search ..................... 251/4, 251/6, 5, 7, 8, 9, 10; 604/34, 250, 251; 138/30, 138/43, 45, 46
See application file for complete search history.

(56) References Cited

U.S. PATENT DOCUMENTS

| 2,726,015 | A | * | 12/1955 | Poock | ........................... 222/98 |
| 5,058,771 | A | * | 10/1991 | Curtis | ........................... 222/99 |
| 5,232,193 | A | | 8/1993 | Skakoon | |
| 5,827,238 | A | | 10/1998 | Kelley | |
| 6,422,529 | B1 | | 7/2002 | Adelberg | |

FOREIGN PATENT DOCUMENTS

| JP | 54108492 A | 8/1979 |
| JP | 03-016570 | 1/1991 |
| JP | 06-109147 | 4/1994 |
| JP | 09-154941 | 6/1997 |

OTHER PUBLICATIONS

Extended European Search Report for Application No. 07002829.5-1526 dated Jun. 1, 2007.

\* cited by examiner

*Primary Examiner*—John K Fristoe, Jr.
*Assistant Examiner*—Andrew J Rost

(57) ABSTRACT

A roller clamp is configured to maintain at a prescribed rate the flow rate of a fluid that flows through a tube. The roller clamp includes a tube winding shaft part around which a fluid flow tube is passed and which prevents the setting of the flow rate being disturbed if the tube is subject to a tensional force.

12 Claims, 5 Drawing Sheets

US 7,810,784 B2

ROLLER CLAMP

FIELD OF THE INVENTION

The present invention generally relates to a roller clamp for regulating the flow rate of a medical fluid which flows through a tube.

BACKGROUND OF THE INVENTION

Conventionally, a fluid transfusion line or a blood transfusion line has been utilized to supply a fluid, such as medicinal liquid or blood, to a patient. In such cases, a flow rate regulator is used to regulate the flow rate of the fluid so that it flows through the tube at the correct speed. For example, Japanese Kokai Patent Application No. Hei 6[1994] 109147, shows flow rate regulators including a roller clamp which utilizes a roller. In the case of said roller clamp, guide grooves are formed on the respective inner surfaces of a pair of side walls provided on either side of a flat bottom plate, and a support shaft is placed across said guide grooves in order to allow the roller to move in the length direction.

In addition, the height between the surface of the bottom plate and the guide grooves is altered at the part along the length direction of the bottom plate, and a planar groove and protruded rows formed along the edge parts of the flat groove are provided on the top surface of the bottom plate along the length of the bottom plate. Then, the position of the roller relative to the bottom plate changes while the tube is placed between the bottom plate and the roller in order to regulate the flow rate of the fluid that flows through the tube.

However, if the tube of the aforementioned conventional roller clamp is pulled abruptly when the patient receiving the fluid rolls over or when a person or an object comes into contact with it, the position of the roller changes, and the flow rate of the fluid that flows through the tube may change.

SUMMARY OF THE INVENTION

In one aspect of the present invention, a roller clamp generally comprises a tube installation part having a bottom part that extends from one side to the other, and a pair of side wall parts on which guide grooves are formed on opposing surfaces that extend upward from either edge part in the length direction of the bottom part in such a way that their heights vary as they extend from one side to the other side. A flow rate regulating roller has a center axis part, which is placed across said pair of side wall parts while being movably supported by said guide grooves at both edge parts. A roller part is provided at the center of said center axis part in the axial direction so that it presses a tube for fluid flow provided at said tube installation part against said bottom part so as to regulate the flow rate of the fluid that flows within said tube as it moves along said guide grooves around said center axis part. A tube winding shaft part winds said tube providing at a part a prescribed distance from the region where said flow rate regulating roller moves, at said tube installation part, along the length direction of said bottom part.

In another aspect, a fluid flow regulator for regulating a fluid flow rate in a tube generally comprises a body including a roller clamp and a tube retaining peg. The tube passes through the roller clamp and around the peg.

Other features will be in part apparent and in part pointed out hereinafter.

BRIEF DESCRIPTION OF THE DRAWINGS

The present invention will now be explained by way of example only with reference to the accompanying drawings in which.

Corresponding reference characters indicate corresponding parts throughout the drawings.

DETAILED DESCRIPTION OF THE DRAWINGS

Figure 1:
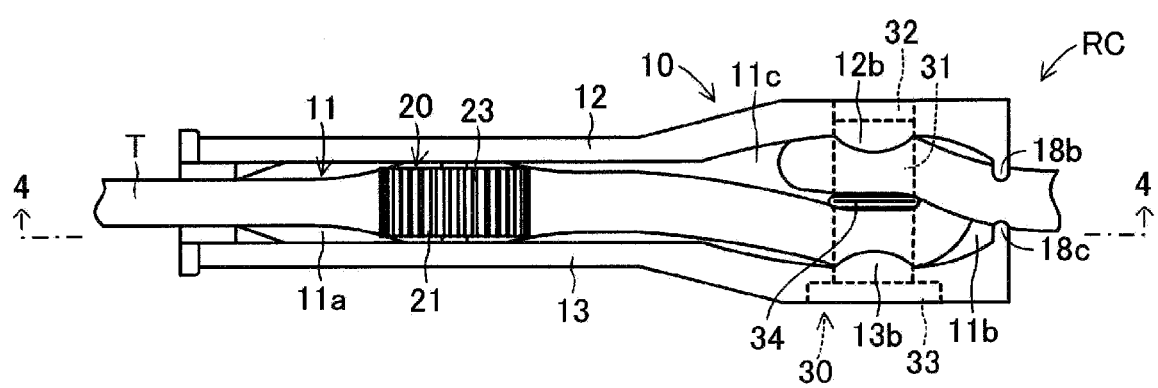
FIG. 1 is a plan view showing the roller clamp pertaining to an embodiment of the present invention.
Figure 2:
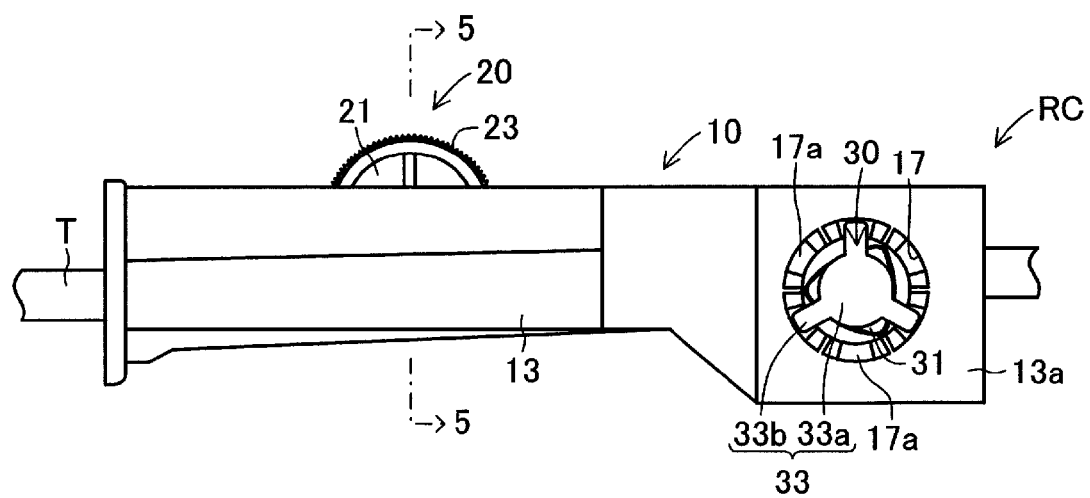
FIG. 2 is a front view of the roller clamp.
Figure 3:
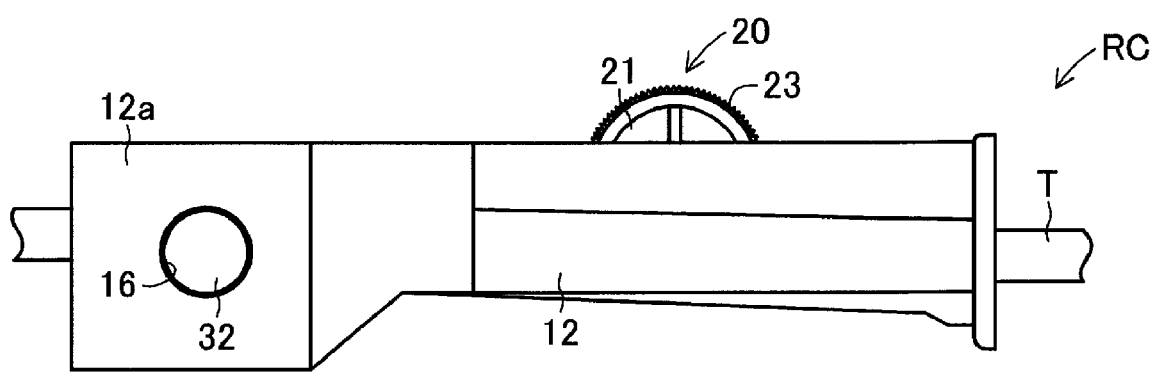
FIG. 3 is a rear view of the roller clamp.

An embodiment of the roller clamp of the present invention will be explained below in detail with reference to the attached figures. FIGS. 1 through 3 show roller clamp RC of this embodiment. Said roller clamp RC is used to regulate the flow rate of a fluid such as a medicinal liquid that flows through tube T. That is, roller clamp RC is configured with flow rate regulating roller 20 which presses tube T against channel-like tube installation part 10 so as to regulate the flow rate of the fluid that flows through tube T and tube winding shaft part 30 that prevents displacement of tube T inside of tube installation part 10 as tube T is wound.

Tube installation part 10 is formed by raising side wall parts 12 and 13 from both edge parts along the length direction of narrow plate like bottom part 11. Part of bottom part 11 extending from the base end part (here, the part corresponding to the upstream side of the fluid that flows through tube T is referred to as the base end side, and the base end side corresponds to the left hand side in FIG. 1 and FIG. 2) to the central part is narrower, and the front end part (right-hand side part in FIG. 1 and FIG. 2) is wider; and tapered part 11c, the width of which increases as it extends from narrower part 11a to wider part 11b, is formed between narrower part 11a at the base end side and wider part 11b at the front end side.

Figure 4:
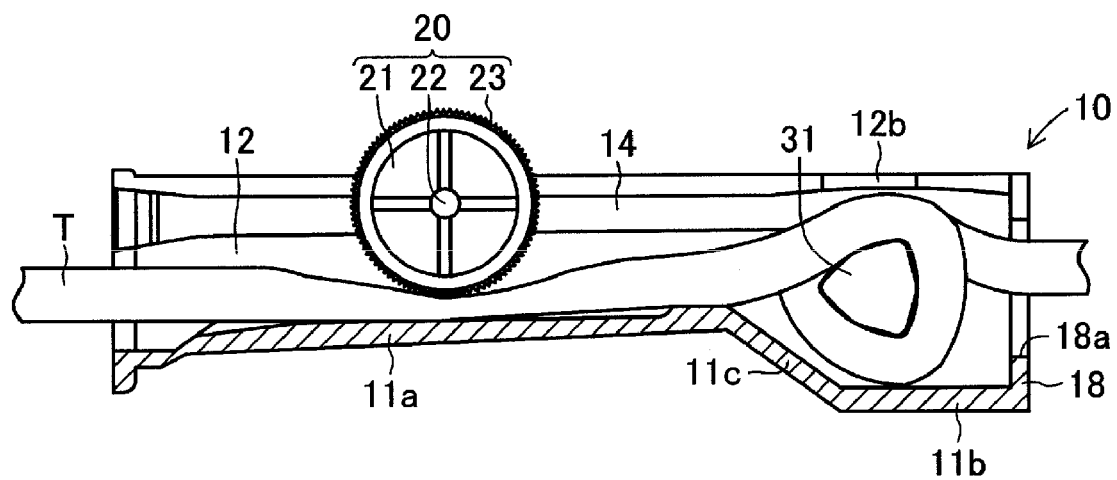
FIG. 4 is a cross section along 4-4 in FIG. 1.

Also, as shown in FIG. 4, narrower part 11a is formed with an upward slope that increases in height as it extends from the base end side to the front end side, and wider part 11b is formed flat below narrower part 11a. Then, tapered part 11c is formed on a sharp declination connecting the front end part of narrower part 11a and the base end part of wider part 11b. In addition, groove part 11d, which increases in height as it extends from the base end side to the front end side along the slope of narrower part 11a, for pressing tube T is formed at the center of the upper surface of narrower part 11a in the width direction.

Side wall parts 12 and 13, formed symmetrically about bottom part 11, are formed straight so that their upper edges are on the same plane. The length of side wall parts 12 and 13 that extends from the base end side to the center part, which corresponds to narrower part 11a of bottom part 11, in the height direction is made shorter; and the length of the front end side, which corresponds to wider part 11b of bottom part 11, in the height direction is made longer. In addition, the parts of side wall parts 12 and 13, which correspond to tapered part 11c of bottom part 11, are provided in such a way that the space between them increases as they extend towards the front end side; and the lower end part is formed on the sloped part formed along the slope of tapered part 11c.

Figure 5:
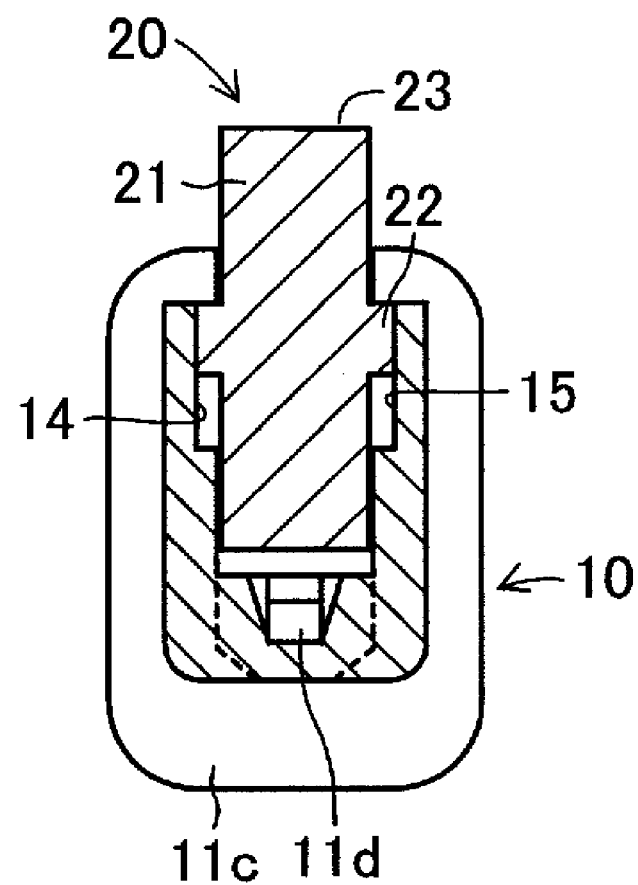
FIG. 5 is a cross section along 5-5 in FIG. 2.

That is, the part of said tube installation part 10 that extends from the base end part to the center part is formed with a narrow channel-like shape, where the lengths in the width and height directions are both made shorter; and the front end part is formed into a short channel-like shape, where a larger bottom part, relative to the lengths in the width and height directions, protrudes downward. Then, as shown in FIG. 4 and FIG. 5, guide grooves 14 and 15 are formed on the opposing inner surfaces of side wall parts 12 and 13. As shown in FIG. 4, guide groove 14 extends from the base end part of side wall part 12 to the front end part along the top edge part of side wall part 12 while maintaining a prescribed distance from the top edge part of side wall part 12. In addition, the region near the base end part of guide groove 14 is formed in such a way that the width in the vertical direction increases slightly as it extends toward the outside.

As described above, because bottom part 11 is formed with a slope whose height increases gradually as it extends from the base end part to the front end part, and guide groove 14 is formed flat, the distance between guide groove 14 and the upper surface of bottom part 11 is greater near the base end side and decreases gradually toward the front end side. Furthermore, although it is not illustrated, guide groove 15 formed on side wall part 13 is formed at a position opposite guide groove 14 and with the same shape as guide groove 14. In addition, supporting hole 16 for holding support shaft 32, which is provided on one side of tube winding shaft part 30, is formed roughly at the center of wider surface 12a which constitutes the front end part of side wall part 12; and hole 17 for attaching rotation stop part 33, which is provided on the other side of tube winding shaft part 30, is formed roughly at the center of wider surface 13a that constitutes the front end part of side wall part 13.

Multiple engagement concave parts 17a are formed at a distance from each other around hole part 17 formed on the surface of wider surface 13a. In addition, retaining protrusion 12b with a curved surface that protrudes toward side wall part 13 is formed at a part above supporting hole 16 formed at the top edge part of wider surface 12a, and retaining protrusion 13b with a curved surface that protrudes toward side wall part 12 is formed at a part above hole part 17 formed on the top part of wider surface 13a.

Then, partitioning part 18 having concave part 18a for allowing tube T to pass is provided at the front end part of tube installation part 10. Top edge part of concave part 18a of said partitioning plate 18 opens to the outside. Then, opposing protrusions 18b and 18c, which approach each other as they extend, are provided at the opened part at the upper center part of partitioning part 18. The distance between said protrusions 18b and 18c is set slightly smaller than the diameter of tube T; thus, tube T can pass through the space between protrusions 18b and 18c by being crushed in the radial direction.

Flow rate regulating roller 20 is configured with disk shaped roller part 21 with a thickness slightly smaller than the space between side wall parts 12 and 13 and center axis part 22 that protrudes to either side of roller part 21 along the center axis of roller part 21. Then, multiple anti-skid protrusions 23, which extend in the axial direction, are formed on the circumferential surface of roller part 21 along the circumferential direction. In addition, the diameter of center axis part 22 is made smaller than the width of guide grooves 14, 15 in the vertical direction. Therefore, flow rate regulating roller 20 can be moved between the base end part and the side part of the front end of tube installation part 10 as it is allowed to move in a small space within the vertical direction inside of tube installation part 10. In addition, although tube T is not shown in FIG. 5 for the sake of explanation, when tube T is attached to roller clamp RC, tube T is placed inside of the space formed between roller part 21 and groove part 11d.

Tube winding shaft part 30 is configured through the provision of support shaft 32 at one end of shaft main body 31 and rotation stop part 33 at the other end. Shaft main body 31 is configured using a rod like shaft with a triangular cross section, where the respective sides bulge outwardly. Then, ring-like protrusion 34, which extends along the circumferential surface of the shaft main body, is formed at the center part of shaft main body 31 in the axial direction. In addition, support shaft 32 is supported by supporting hole 16 of side wall part 12 in such a way that it can be rotated. Rotation stop part 33 is configured using three engagement protrusions 33b, which are provided at regular intervals on the outer circumference of the front end part of shaft part 33a with the same diameter as that of support shaft 32.

Respective engagement protrusions 33b are placed on the outside of hole part 17 of side wall part 13 and can engage with respective multiple engagement concave parts 17a formed on the circumference of hole part 17. Therefore, tube winding shaft part 30 can be attached to tube installation part 10 by inserting support shaft 32 into hole part 17 from the side of side wall part 13 and by engaging with respective engagement protrusions 33b with engagement concave parts 17a. In addition, respective protrusions 33b and engagement concave parts 17a can be engaged in different positions. Furthermore, both edge parts of tube T that overlap when tube T is wound on shaft main body 31 of said tube winding shaft part 30 are prevented from falling off of tube installation part 10 by retaining protrusions 12b and 13b. Here, the overlapping parts of tube T are guided to either side of shaft main body 31 by protrusion 34.

In the case of roller clamp RC configured in said manner, a prescribed amount of tube T is wound on shaft main body 31 during the manufacturing process. At this time, as this prescribed amount of tube T is wound tightly around shaft main body 31, the portion wound around shaft main body 31 is placed on either side of shaft main body 31 across protrusion part 34. Then, when roller clamp RC is to be used, the upstream end of tube T is connected to a container housing a medicinal liquid, and the downstream end of tube T is connected to a centesis element, such as an self-retaining needle, which has been inserted into the body of a patient.

Next, after the medicinal liquid is allowed to flow into tube T from the container, and the air in tube T is expelled, flow rate regulating roller 20 is placed at the side of the front end part of tube installation part 10 so as to stop the flow of the medicinal liquid. The centesis element punctures the patient's body at the prescribed location under said condition, and roller 20 is moved gradually toward the side of base end part of tube installation part 10 in order to correctly adjust the flow rate of the medicinal liquid in tube T. Then, the slack between flow rate regulating roller 20 on tube T and tube winding shaft part 30 is taken up so that the part of tube T wound around shaft main body part 31 is not too taut or too loose.

Here, tube winding shaft part 30 can be rotated as needed with tube winding shaft part 30 pulled slightly outward so as to release the engagement between respective engagement protrusions 33b and engagement concave parts 17a. As a result, a fixed amount of medicinal liquid can be supplied from the container to the patient. Even if tube T is pulled as the patient moves carelessly while the medicinal liquid is being supplied to the patient, the force applied to tube T is stopped at tube winding shaft part 30 without reaching flow rate regulating roller 20.

Thus, the flow rate of the medicinal liquid is reduced only temporarily, and the flow rate of the medicinal liquid returns to the original flow rate as the pulling force applied to tube T is released. In addition, to change the flow rate of the medicinal liquid that flows into tube T, flow rate regulating roller 20 is moved to the position at which the intended flow rate is attained. Then, the extent to which tube T is pulled is adjusted in such a way that flow rate regulating roller 20 does not move easily even if tube T is pulled.

As described above, with respect to roller clamp RC of the present embodiment, the flow rate of the medicinal liquid that flows through tube T can be adjusted by changing the position of flow rate regulating roller 20 relative to tube installation part 10, and the part sandwiched between bottom part 11 of tube installation part 10 and flow rate regulating roller 20, and flow rate regulating roller 20 is prevented from being displaced by winding tube T around shaft main body 31 of tube winding shaft part 30. Thus, the medicinal liquid can be allowed to flow through tube T reliably.

In addition, even if tube T is pulled abruptly, only the part of tube T wound around tube winding shaft part 30 becomes temporarily constricted as it is stretched, but flow rate regulating roller 20 and the position of tube T hardly change. Furthermore, tube winding shaft part 30 is allowed to rotate, and respective engagement protrusions 33b engage with respective engagement concave parts 17a in order to allow roller clamp RC to be fixed at a prescribed position. Thus, tube T moves easily along roller clamp RC.

In addition, because tube winding shaft part 30 on which tube T is wound can be fixed at said position, the unintentional rotation of tube winding shaft part 30 can be eliminated. Furthermore, because shaft main body 31 has an approximately triangular cross section, the friction generated between tube winding shaft part 30 and tube T increases, so that the displacement of tube T is eliminated. In addition, because tube winding shaft part 30 is provided closer to the patient than to flow rate regulating roller 20 at tube installation part 10, flow rate regulating roller 20 and tube T are even less likely to be displaced, so that the flow rate through tube T is less likely to change.

In addition, the roller clamp is not restricted to the aforementioned embodiment; it can be modified as needed when implemented. For example, although the end part of tube T on the side of tube winding shaft part 30 side is extended on the side of the patient, and the end part of flow rate regulating roller 20 on tube T is extended on the container side where the medicinal liquid is held in the aforementioned embodiment, the directions may be reversed. Here, too, because tube T is wound around tube winding shaft part 30, flow rate regulating roller 20 and tube T are less likely to be displaced.

In addition, tube winding shaft part 30 may be configured to be rotatable instead of providing engagement protrusions 33b and respective engagement concave parts 17a. In this way, the application of a large force to tube T can be prevented if tube T is pulled. That is, because tube winding shaft part 30 rotates when tube T is pulled, tube T is never stretched very much, which would otherwise occur if a high force were applied to it, so that tube T can be prevented from being destroyed. In addition, because stretched tube T returns to its original condition as the force pulling tube T is released, the flow rate of the medicinal liquid that flows through tube T returns to the prescribed flow rate.

Here, too, because tube T engages with flow rate regulating roller 20 and tube winding shaft part 30, the flow rate of the fluid that flows through tube T never changes unless the part engaged with flow rate regulating roller 20 and the part engaged with tube winding shaft part 30 are both displaced. In addition, although tube winding shaft part 30 is placed across side wall parts 12 and 13 in the aforementioned embodiment, said tube winding shaft part may be configured using a shaft body that extends upward from bottom part 11.

Here, too, the tube winding shaft part may be fixed, or it may be made rotatable. Furthermore, although shaft main body 31 has an approximately triangular cross section in the aforementioned embodiment, the cross section need not be triangular. Besides being triangular, shaft main body 31 may also be a circular or in the shape of a polygon having more than three angles. Furthermore, although the fluid was a medicinal liquid in the aforementioned embodiment, said fluid can be any fluid as long as it is a therapeutic fluid to be supplied to a patient; for example, it may be a nutritional supplement or blood. In addition, the configuration of the parts other than the aforementioned part of said roller clamp can be modified arbitrarily without deviating from the technical scope of the present invention.

In the illustrated embodiment, the roller clamp can maintain at a prescribed rate the flow rate of the fluid that flows through the tube.

The roller clamp pertaining to the illustrated embodiment of the present invention comprises a tube installation part, having a bottom part that extends from one side to the other, and a pair of side wall parts on which guide grooves are formed on opposing surfaces that extend upward from either edge part in the length direction of the bottom part in such a way that their heights vary as they extend from one side to the other side, and a flow rate regulating roller having a center axis part, which is placed across the pair of side wall parts while being movably supported by the guide grooves at both edge parts, and a roller part, which is provided at the center of the center axis part in the axial direction, whereby it presses a tube for fluid flow provided at the tube installation part against the bottom part so as to regulate the flow rate of the fluid that flows through the tube as it moves along the guide grooves around the center axis part, a tube winding shaft part for winding the tube is provided at a part at a prescribed distance from the region the flow rate regulating roller moves at the tube installation part along the length direction of the bottom part.

As described above, in the case of the roller clamp configured in the aforementioned manner pertaining to the present invention, the length in the height direction between the bottom part of the tube installation part and the guide grooves formed on the side wall parts changes as it extends from one side to the other side so as to change the position of the flow rate regulating roller with respect to the bottom part of the tube installation part in order to regulate the flow rate of the fluid that flows through the tube. In addition, the tube is wound around the tube winding shaft part in order to prevent the position of the tube sandwiched between the bottom part of the tube installation part and the flow rate regulating roller and that of the flow rate regulating roller from shifting. Thus, the prescribed amount of fluid set for the tube can flow through the tube.

In addition, the tube to which the roller clamp is to be attached is provided between a container that holds a medical fluid and the patient to whom the fluid is supplied, and the roller clamp is attached to the tube while the tube winding shaft part is placed closer to the patient than the flow rate regulating roller of the installation part. Thus, when the tube is pulled from its position close to the patient, the pulling force is first absorbed by the part of the tube winding shaft part on which the tube is wound, so that the pulling force becomes less likely to reach the part sandwiched between the bottom part of the tube installation part and the flow rate regulating roller. Thus, the flow rate regulating roller and the tube are less likely to become displaced, thereby preventing the flow rate of the tube from changing.

In addition, even if the tube is pulled abruptly, only the part of the tube that is wound around the tube winding shaft part or the part sandwiched between the bottom part of the tube installation part and the flow rate regulating roller becomes thinner as it is stretched, but the positions of the flow rate regulating roller and the tube are less likely to be displaced. That is, when the part of the tube that is wound around the tube winding shaft part is pulled toward the outside of the roller clamp, the flow rate of the fluid that flows through the tube decreases as the part that is wound around the tube winding shaft part becomes thinner. However, the tube returns to its original state as the tube becomes free from the pulling force, and the flow rate of the fluid returns to the prescribed flow rate. Thus, the part of the tube sandwiched between the bottom part and the flow rate regulating roller is completely unaffected.

Because the roller clamp is configured in said manner, the flow rate of the fluid that flows through the tube is maintained at the prescribed flow rate unless an exceptionally large force is applied to the tube. That is, because the tube is fitted between the bottom part of the tube installation part and the flow rate regulating roller and around the circumference of the tube winding shaft part, the flow rate of the fluid that flows through the tube never changes unless the position of the part fitted between the bottom part of the tube installation part and the flow rate regulating roller and the position of the part fitted to the circumference of the tube winding shaft part are both shifted. In addition, the tube winding shaft part of the present invention may be placed across both side wall parts, or they may be extended upwards from the bottom part of the tube installation part. In addition, the tube winding shaft part may be fixed with respect to the tube installation part, or it may be attached to the tube installation part so that it can rotate about the shaft axis.

A structural feature of the roller clamp pertaining to the illustrated embodiment of the present invention is that the tube winding shaft part is provided in such a way that it can rotate about the shaft axis. As such, operation of moving the roller clamp along the tube becomes easy.

Another structural feature of the roller clamp pertaining to the illustrated embodiment of the present invention is that the tube winding shaft part can be fixed in a prescribed position in the direction of rotation. Thus, because the tube winding shaft part can be fixed at a prescribed position in the direction of rotation, the tube winding shaft part never rotates unexpectedly, so that the displacement of the tube can be prevented.

In addition, another structural feature of the roller clamp pertaining to the illustrated embodiment of the present invention is that the part where the tube is wound on the tube winding shaft part has a triangular or circular cross section. Although the cross section of the part of the tube winding shaft part on which the tube is wound can be formed with a quadrangular or a polygonal shape, a triangular or circular shape is preferred. If the cross section of the part of the tube winding shaft part on which the tube is wound is triangular, the friction generated between the tube winding shaft part and the tube increases, so that an improved roller clamp that prevents displacement of the tube can be obtained. In addition, if the cross section of the part of the tube winding shaft part on which the tube is wound is circular, the tube is easily wound, and the wound part of the tube is less likely to deform.

Having described the illustrated embodiment of the invention in detail, it will be apparent that modifications and variations are possible without departing from the scope of the invention defined in the appended claims.

When introducing elements of the present invention or the illustrated embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A roller clamp comprising:
   a tube installation part having a bottom part that extends from one side to the other, and a pair of side wall parts on which guide grooves are formed on opposing surfaces that extend upward from either edge part in the length direction of the bottom part in such a way that their heights vary as they extend from one side to the other side;
   a flow rate regulating roller having a center axis part, which is placed across said pair of side wall parts while being movably supported by said guide grooves at both edge parts;
   a roller part, which is provided at the center of said center axis part in the axial direction so that it presses a tube for fluid flow provided at said tube installation part against said bottom part so as to regulate the flow rate of the fluid that flows within said tube as it moves along said guide grooves around said center axis part; and
   a tube winding shaft part for winding said tube providing at a part a prescribed distance from the region where said flow rate regulating roller moves, at said tube installation part, along the length direction of said bottom part, wherein said tube winding shaft part can rotate.

2. The roller clamp of claim 1 wherein said tube winding shaft part can be fixed at a prescribed position in the direction of rotation.

3. The roller clamp of claim 1 wherein the part where said tube is wound on said tube winding shaft part has a triangular or circular cross section.

4. A fluid flow regulator for regulating a fluid flow rate in a tube comprising a body incorporating a roller clamp and a tube retaining peg, wherein said tube passes through said roller clamp and around said peg, wherein said peg is rotatable in said body, and wherein the regulator is configured to regulate fluid delivery from a container to a patient such that the fluid flows in the tube from the container around the retaining peg and to the patient.

5. The fluid flow controller according to claim 4 wherein said peg has a round cross-section.

6. The fluid flow controller according to claim 4 wherein said peg has a rounded triangle cross-section.

7. The fluid flow controller according to claim 4 wherein said tube retaining peg provides tensional isolation between a tensional force applied to said tube and said roller clamp.

8. The fluid flow controller according to claim 4 wherein said controller further comprises an actuating member attached to said rotatable peg.

9. The fluid flow controller according to claim 8 wherein said body comprises a beveled ring arranged to interact with said actuating member to restrain free rotation of said rotatable peg.

10. The fluid flow controller as set forth in claim 4 wherein the body has an opening generally on the opposite side of the retaining peg from the roller clamp for passage of the tube out of the body.

11. The fluid flow controller as set forth in claim 4 wherein the body comprises a narrower part and a wider part, the roller clamp being disposed in the narrower part and the retaining peg being disposed in the wider part for permitting the tube to be wound around the retaining peg.

12. The fluid flow controller as set forth in claim 4 wherein the retaining peg has a ring-like protrusion thereon positioned to guide parts of the tube wound on the retaining peg to either side of the protrusion.

\* \* \* \* \*